United States Patent
Sarkar

(10) Patent No.: US 6,774,232 B2
(45) Date of Patent: Aug. 10, 2004

(54) LOW COLOR, LOW SODIUM BENZOXAZINONE UV ABSORBERS AND PROCESS FOR MAKING SAME

(75) Inventor: Asim K. Sarkar, Brasschaat (BE)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 10/209,436

(22) Filed: Jul. 31, 2002

(65) Prior Publication Data

US 2003/0096889 A1 May 22, 2003

Related U.S. Application Data

(60) Provisional application No. 60/331,088, filed on Oct. 22, 2001.

(51) Int. Cl.[7] ............................................. C07D 265/06
(52) U.S. Cl. ....................................................... 544/92
(58) Field of Search ........................................... 544/92

(56) References Cited

U.S. PATENT DOCUMENTS 3,989,698 A    11/1976  Jacobs et al. ............ 260/244 A
4,446,262 A    5/1984   Okumura et al. ............. 524/89

FOREIGN PATENT DOCUMENTS

| DE | 4101380 A | 7/1992 |
| WO | WO93/22300 A | 11/1993 |
| WO | WO98/19862 A | 5/1998 |
| WO | WO99/48878 A | 9/1999 |

OTHER PUBLICATIONS

"Standard Test Method for Indexes of Whiteness and Yellowness of Near–White, Opaque Materials," ASTM, E 313–73 (Reapproved 1987), pp. 279–282.

*Primary Examiner*—Richard L. Raymond
(74) *Attorney, Agent, or Firm*—James A. Jubinsky; Fran Wasserman; Claire M. Schultz

(57) ABSTRACT

The present invention relates to benzoxazinone compounds having a yellow index less than about 0, and a sodium concentration less than about 50 ppm. This invention also relates to a process for preparing these compounds comprising the step of reacting an isatoic anhydride with approximately stoichiometric amounts of an acylating compound, where the isatoic anhydride is purified by re-crystallization or other purification methods.

21 Claims, No Drawings

LOW COLOR, LOW SODIUM BENZOXAZINONE UV ABSORBERS AND PROCESS FOR MAKING SAME

This application claims the benefit under 35 U.S.C. §119(e) of U.S. Provisional Application Ser. No. 60/331,088, filed Oct. 22, 2001.

FIELD OF THE INVENTION

This invention relates to improved benzoxazinone UV absorbers. More specifically, this invention relates to low color, low sodium benzoxazinone UV absorbers especially suitable for high transparency applications, and the process for making such absorbers.

BACKGROUND OF THE INVENTION

Exposure to sunlight and other sources of ultraviolet (UV) radiation is known to cause degradation of a wide variety of materials, especially polymeric materials. For example, polymeric materials such as plastics often discolor and/or become brittle as a result of prolonged exposure to UV light due primarily to a reduction in the molecular weight of the polymer. Accordingly, a large body of art has been developed directed towards materials such as UV light absorbers and stabilizers, which are capable of inhibiting such degradation.

One important application that uses UV absorbers is optical quality lenses, such as prescription eyewear. Preferably, polycarbonates are used in lenses due to their toughness and transparency over acrylics and other amorphous polymers. Clarity and color are important parameters in this application and absorbers are needed to screen UV light up to the 380 nm region without affecting the visible region over 400 nm. Some benzoxazinone UV absorbers, such as 2,2,-p-phenylenebis(3,1-benzoxazine-4-one), are preferred in this application because they meet these UV requirements.

However, commercial benzoxazinone compounds like 2,2'-p-phenylenebis(3,1-benzoxazine-4-one) have problems due to their method of manufacturing. These methods are disclosed in U.S. Pat. Nos. 3,989,698 and 4,446,262.

One method of producing 2,2'-p-phenylenebis(3,1-benzoxazine-4-one) is by reacting anthranilic acid, sodium carbonate, terephthaloyl dichloride and acetic anhydride (example 19 in U.S. Pat. No. 4,446,262). However, this method results in a high concentration of sodium ion ($Na^+$) impurities in the benzoxazinone product, which severely degrades polycarbonates.

Another method to produce 2,2'-p-phenylenebis(3,1-benzoxazine-4-one) is by reacting isatoic anhydride with terephthaloyl dichloride (Example 24 in U.S. Pat. No. 3,989,698). However, a problem with prior art commercial products using this method is that they have a high degree of color that limits their desirability to be used in optical lens and other high transparency applications.

Therefore, there is a need to produce a low color, low sodium benzoxazinone compound, which is suitable for use in high transparency and other polymeric applications.

SUMMARY OF THE INVENTION

The present invention relates to a compound of Formula I:

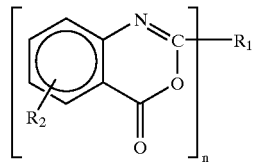

Formula I where n is 1 to 3, $R_1$ is a direct bond or a hydrocarbon residue having a valence of n which may further contain a heteroatom, and $R_2$ is hydrogen, halo, nitro, $C_1$ to $C_8$ alkyl, $C_1$ to $C_8$ alkoxy, or $C_1$ to $C_8$ alkenyloxy. These compounds have a yellow index less than about 0 and a sodium concentration less than about 50 ppm.

This invention also relates to a process for preparing the compound of Formula I comprising the step of reacting an isatoic anhydride with approximately stoichiometric amounts of an acylating compound, where the isatoic anhydride is purified by re-crystallization or other purification methods.

DETAILED DESCRIPTION OF THE INVENTION

The present invention relates to a compound of Formula I:

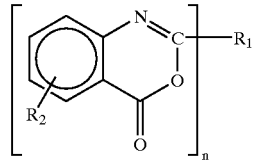

Formula I where n is 1 to 3, $R_1$ is a direct bond or a hydrocarbon residue having a valence of n which may further contain a heteroatom, and $R_2$ is hydrogen, halo, nitro, $C_1$ to $C_8$ alkyl, $C_1$ to $C_8$ alkoxy, or $C_1$ to $C_8$ alkenyloxy, and where said compound has a yellow index less than about 0 and a sodium concentration less than about 50 ppm.

In the present invention, isatoic anhydride also includes its diacid.

Preferably, the compounds of Formula I have a yellow index less than about −5 and more preferably less than about −10.

Also, preferably, the compound of Formula I has a sodium concentration less than about 20 ppm, more preferably less than about 10 ppm and preferably less than about 5 ppm or less than about 1 ppm.

The above compound may be used as UV stabilizers for polymeric systems, especially for those used in the high transparency optical systems.

The aromatic residue, $R_1$, may be any hydrocarbon residue having a valence of n and may be a direct bond when n is 2. The hydrocarbon residue may further contain a heteroatom.

When n is 1, $R_1$ may include substituted or unsubstituted aliphatic groups containing 1 to 18 carbon atoms, substituted or unsubstituted aromatic groups having 6 to 18 carbon atoms, or substituted or unsubstituted alicyclic groups having 5 to 18 carbon atoms. Examples of aliphatic groups are methyl, ethyl, propyl, butyl, pentyl, hexyl, decyl, octadecyl, and the like. Examples of aromatic groups are phenyl, naphthyl, biphenyl, tolyl, methyinaphthol, nitrophenyl, acetylphenyl and chlorophenyl. Examples of alicyclic groups are cyclopentyl and cyclohexyl.

When n is 2, $R_1$ may include substituted or unsubstituted aliphatic residues containing 1 to 18 carbon atoms, substituted or unsubstituted aromatic residues having 6 to 18 carbon atoms, or substituted or unsubstituted alicyclic residues having 5 to 18 carbon atoms. Examples of aliphatic groups are methylene, ethylene, propylene, butylene, pentylene, hexylene, decylene, octadecylene, and the like. Examples of aromatic groups are phenylene, naphthylene, biphenylene, tolylene, xylenylene, methylnaphthylene, nitrophenylene, acetylphenylene and chlorophenylene. Examples of alicyclic residues are cyclopentylene and cyclohexylene. Preferably, when n is 2, $R_1$ is a phenylene, diphenylene or a naphthylene and more preferably para-phenylene.

When n is 3, any suitable trivalent hydrocarbon residue may be used for $R_1$. It is preferred that the hydrocarbon residue is a trivalent aromatic residue.

Specific examples of the compounds of Formula I are: 2-Methyl-3,1-benzoxazin-4-one, 2-butyl-3,1-benzoxazin-4-one, 2-phenyl-3,1-benzoxazin-4-one, 2-(1- or 2-naphthyl)-3,1-benzoxazin-4-one, 2-(4-biphenyl)-3,1-benzoxazin-4-one, 2-p-nitrophenyl-3,1-benzoxazin-4-one, 2-m-nitrophenyl-3,1-benzoxazin-4-one, 2-p-benzoylphenyl-3,1-benzoxazin-4-one, 2-p-methoxyphenyl-3,1-benzoxazin-4-one, 2-O-methoxyphenyl-3,1-benzoxazin-4-one, 2-cyclohexyl-3,1-benzoxazin-4-one, 2-p-(or m-)phthalimidephenyl-3,1-benzoxazin-4-one, N-phenyl -4-(3,1-benzoxazin-4-one-2-yl)phthalimide, N-benzoyl-4-(3,1-benzoxazine-4-one-2-yl)aniline, N-benzoyl-N-methyl-4-(3,1-benzoxazin-4-one-2-yl)-aniline, 2-[p-(N-phenylcarbamonyl)phenyl]-3,1-benzoxazin-4-one, and 2-[p-(N-phenyl N-methylcarbamoyl)phenyl]-3,1-benzoxazin-4-one. 2,2'-bis(3,1-benzoxazin-4-one), 2,2'-ethylenebis(3,1-benzoxazin-4-one), 2,2'-tetramethylenebis(3,1-benzoxazin-4-one), 2,2'-hexamethylenebis(3,1-benzoxazin-4-one), 2,2'-decamethylenebis(3,1-benzoxazin-4-one), 2,2'-p-phenylenebis(3,1-benzoxazin-4-one), 2,2'-m-phenylenebis(3,1-benzoxazin-4-one), 2,2'-(4,4'-diphenylene)bis(3,1-benzoxazin-4-one), 2,2'-(2,6-or 1,5-naphthalene)bis(3,1-benzoxazin-4-one), 2,2'-(2-methyl-p-phenylene)bis(3,1-benzoxazin-4-one), 2,2'-(2-nitro-p-phenylene)bis(3,1-benzoxazin-4-one), 2,2'-(2-chloro-p-phenylene)bis(3,1-benzoxazin-4-one), 2,2'-(1,4-cyclohexylene)bis(3,1-benzoxazin-4-one), N-p-(3,1-benzoxazin-4-on-2-yl)phenyl, 4-(3,1-benzoxazin-4-on-2-yl)phthalimide, and N-p-(3,1-benzoxazin-4-on-2-yl)benzoyl, 4-(3,1-benzoxazin-4-on-2-yl)aniline, 1,3,5-tri(3,1-benzoxazin-4-on-2-yl)benzene, 1,3,5-tri(3,1-benzoxazin-4-on-2-yl)naphthalene, and 2,4,6-tri(3,1-benzoxazin-4-on-2-yl)naphthalene.

As indicated earlier, the compounds of Formula I are particularly useful as ultraviolet light absorber agents for stabilizing a wide variety of materials including, for example, various polymers (both cross-linked and thermoplastic), optical lenses, photographic materials, dye solutions for fiber and textile materials, as well as in ultraviolet light screening agents (such as sunscreens). The compounds of Formula I may be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the compounds of Formula I may be employed to stabilize materials which are subject to degradation by ultraviolet radiation by incorporating the presently claimed compounds into a composition comprising polymeric or other materials, either chemically or physically. Non-limiting examples of materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfides, PPO, polysulfones, polyethersulfones, polyvinylchlorides, polycarbonates, polyketones, aliphatic polyketones, thermoplastic TPO's, aminoresin cross-linked polyacrylates and polyesters, polyisocyanate cross-linked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, fibers, inks, and blends thereof.

Preferably, the polymer material is substantially transparent to visible light. Articles, which permit transmission of at least about 75% of incident light, are regarded as being substantially transparent to visible light. For example, transparent molded articles based on amorphous resins or thin transparent molded articles based on crystalline resins, for example films, sheets, lenses, plates, tubes or pipes of polycarbonates, sheets films, bottles of polyethylene terephthalate, polyethylene terephthalate copolyesters, or wholly aromatic polyesters, sheets or films of polyvinyl chloride, films of polypropylene, sheets or films of polyethylene, and sheets or films of methacrylate resins are preferably used with the compounds of Formula I.

The amount of the compounds of Formula I incorporated in the material to be stabilized is about 0.001 to about 20%, preferably about 0.01 to about 15%, and more preferably about 0.02 to about 10% by weight.

This invention further contemplates the addition of other additives to the compounds of Formula I and the material to be stabilized. Examples of these additives include, but are not limited to: anti-oxidants; other UV absorbers and stabilizers such as 2-(2'-hydroxyphenyl)benzotriazoles, oxamides, 2-(2-hydroxphenyl)-1,3,5-triazines, 2-hydroxybenzophenones, sterically hindered amines, nickel compounds, cinnamates, benzylidene malanates, and hindered benzoates; metal deactivators; hydroxylamines; nitrones; co-stabilizers; nucleating agents; clarifying agents; neutralizers; metallic stearates; metal oxides; hydrotalcites; fillers and reinforcing agents; plasticizers; lubricants; emulsifiers; pigments; rheological additives; catalysts; level agents; optical brighteners; flameproofing agents; anti-static agents; blowing agents and combinations thereof.

Preparation of Benzoxazinone Compounds of the Present Invention

The preparation of the benzoxazinone compounds of Formula I is performed similar to the method of Examples 1–18 of U.S. Pat. No. 4,446,262. However, before the isatoic anhydride is used, it is first purified by any suitable method such as re-crystallization sublimation or extraction. The preferred method is re-crystallization whereby the isatoic anhydride is dissolved at elevated temperatures in a suitable solvent such as pyridine, dimethylformamide (DMF), dimethyl sulfoxide (DMSO), dimethyl acetamide (DMAC), ethers such as tetrahydrofuran (THF), and chlorinated solvents such as methylene chloride. The mixture is allowed to cool, filtered and dried to obtain a purified isatoic anhydride.

It has been discovered that the purification of the isatoic anhydride results in a product that is less yellow and has a lower sodium concentration than prior art products. Both low color and low sodium levels are important parameters when the benzoxazinone compounds are used in transparent materials, such as polycarbonates.

The purified isatoic anhydride is then at least partially dissolved or suspended in any suitable reaction medium, such as pyridine or dimethylformamide, at temperatures of about 25 to about 75° C. Preferably, the reaction medium wholly or at least partially contains an organic base. The preferred organic base is a tertiary amine. An approximately stoichiometric amount of an acylating compound is then slowly added to the isatoic anhydride mixture. Examples of preferred acylating compounds are carboxylic acid anhydrides and acyl halides. The preferred acylating compound is acyl halides. The mixture is then heated under reflux for 3 to 5 hours and then cooled to room temperature or below. The precipitated crystals are then separated by filtration, washed and dried. The resulting crystals may then be recrystallized using any suitable solvent such as toluene to give the final benzoxazinone product.

Preferably, the amount of the reaction medium used in the reaction is about 0.1 to about 30 parts by weight to 1 part of the isatoic anhydride present in the reaction mixture, more preferably about 1 to about 20 parts by weight, even more preferably about 5 to about 15 parts by weight of the reaction medium to 1 part of the isatoic anhydride.

The preferred tertiary amine solvents include the various substituted and unsubstituted aliphatic, aromatic and cyclic tertiary amines have up to about 20 carbon atoms. Examples include the pyridines and quinolines such as, for example, benzyl pyridine, butyl pyridine, phenyl pyridine, propyl pyridine, methoxy pyridine, trimethyl quinoline, phenyl quinoline, methyl quinoline, benzyl quinoline, methoxyquinoline and various combinations thereof. In addition to pyridine, the homologs of pyridine may be used which includes the methyl pyridines or picolines, dimethyl pyridine, ethyl pyridine, trimethyl pyridine, 5-ethyl-2-methyl pyridine, diethyidimethyl pyridine etc. Various other tertiary amines that may be used include, for example, dimethylethyl amine, triphenyl amine, methyldiethyl amine, tripropyl amine, trimethyl amine, triethyl amine, triamyl amine, tributyl amine and various other aliphatic or cycloaliphatic tertiary amines. Other amines that may be used include the dialkyl toluidines such as dimethyl toluidine, the N,N-dialkylanilines such as N,N-dimethyl aniline, N,N-diethyl aniline, etc., the N-substituted alkyl pyrrolines such as methyl pyrroline, ethyl pyrroline, etc., the N-substituted alkyl pyrroles such as methyl pyrrole, ethyl pyrrole etc., the N-substituted alkyl piperidines, the N-substituted alkyl piperazines and various other tertiary amines and combinations thereof in any proportion.

As mentioned previously, the preferred acylating agents used in the process of the present invention include carboxylic acid anhydrides and acyl halides.

The prefered carboxylic acid anhydrides include the saturated or unsaturated aliphatic, cycloaliphatic or aromatic anhydrides. These anhydrides may have substituted or unsubstituted mono- or divalent organic radicals with up to 30 carbon atoms. More specifically, the carboxylic acid anhydrides include the saturated acid anhydrides such as acetic, propionic and butyric anhydride, etc. The unsaturated acid anhydrides include acrylic, substituted acrylic, crotonic and oleic anhydride, etc. The aromatic carboxylic acid anhydrides include, for example, phenylacetic anhydride, phthalic anhydride, and benzoyl phthalic anhydride, etc. An illustration of other anhydrides include chloroacetic anhydride, caproic anhydride, caprylic anhydride, palmitic anhydride, phenoxyacetic anhydride, lauric anhydride, heptylic anhydride, myristic anhydride, stearic anhydride, sulfobenzoic anhydride, valeric anhydride, benzoic anhydride, benzoyl acetic anhydride, nitrophthalic anhydride, tetrahydrophthalic anhydride, cinnamic anhydride, 2-nitrocinnamic anhydride, naphthenic anhydride, 3-cyclohexene-1,2-dicarboxylic anhydride, and the like.

The preferred acyl halides include for example, the acyl mono- and dihalides, i.e. chlorides, bromides, iodides and fluorides, such as the benzoyl halides, i.e. benzoyl chloride, benzoyl bromide, benzoyl fluoride, benzoyl iodide, the acetyl halides such as acetyl chloride, acetyl bromide, acetyl iodide, acetyl fluoride and various haloacetyl chlorides such as bromoacetyl chloride, chloroacetyl chloride, etc. Other acyl halides include halobenzoyl halides such as chlorobenzoyl chloride, bromobenzoyl chloride and various substituted benzoyl halides such as nitrobenzoyl chloride or bromide, etc. In addition, other acyl halides include myristyl chloride, palmityl chloride, pelargonyl chloride, phenylacetyl chloride, propionyl chloride, butyryl chloride, capryl chloride, lauryl chloride, crotonyl chloride, valeryl chloride, naphthyl chloride, stearyl chloride and the dihalides such as succinyl dichloride or dibromide, phthalyl dichloride, isophthalyl dichloride, terephthaloyl dichloride, 4,4'-diphenyidicarboxylic acid dichloride and naphthalene-2,6-dicarboxylic acid dichloride oxalyl dichloride or dibromide, pivaloyl dichloride, cinnamoyl chloride, etc. As an example, these carboxylic acid halides may be prepared by reacting the acid or its anhydride by known methods with a halogenating agent such as phosphorous trichloride or tribromide, phosphorous pentachloride, thionyl chloride, etc.

Yellow Index Measurement Procedure

The Yellow Index (YI) is measured using a COLOR-EYE® 7000 spectrophotometer supplied by MACBETH® a Division of Kollmorgen Instrument Corporation. The sample crystals of the benzoxazinone compounds are placed in a 1 cm thick curvette. The curvette is tapped to settle the crystals and eliminate void spaces. Additional crystals are added to refill the curvette. This is repeated as necessary to obtain a void free curvette. The curvette is placed in the spectrophotometer and the CIELab system parameters (L, a, b) are measured. The YI is calculated from the measured CIELab system parameters using ASTM E313-73. The measurements with the spectrophotometer are made relative to a factory calibrated and installed ceramic tile standard. High YI values indicate the sample is more yellow. For most applications, lower or negative YI numbers are preferred.

EXAMPLES

Certain embodiments and features of the invention are illustrated, and not limited, by the following working examples.

Example 1

Preparation of Low YI, Low Sodium 2,2'-p-phenylenebis(3,1-benzoxazine-4-one)

Commercial isatoic acid from BASF Corporation was re-crystallized by dissolving it at a temperature of 60° C. in dimethylformamide (DMF). The mixture was allowed to cool, the crystals filtered and dried to obtain a purified isatoic anhydride.

One part purified dry isatoic anhydride was then dissolved in 10 parts dry pyridine at a temperature of approximately 60° C. Terephthaloyl dichloride (0.63 parts) from E. I. du Pont de Nemours and Company was slowly added with stirring to the isatoic anhydride mixture with slight cooling to maintain the temperature. This mixture was then heated to reflux for approximately 4 hours. The reaction was then cooled to room temperature. The precipitated product was filtered, washed and dried to give the final 2,2'-p-phenylenebis(3,1-benzoxazinone) product.

Comparison Example 1A—Preparation of 2,2'-p-phenylenebis(3,1-benzoxazine-4-one) Without Purified Isatoic Anhydride A sample of 2,2'-p-phenylenebis(3,1-benzoxazinone) was prepared without purifying the isatoic anhydride according to the procedure in Example 1 above.

Comparison Example 1B—Preparation of 2,2'-p-phenylenebis(3,1-benzoxazine-4-one) Utilizing Anthranilic Acid Anthranilic acid (1 part by weight) and 0.35 parts of NaOH were dissolved in approximately 5.5 parts of methyl isobutyl ketone (MIBK). With stirring, a solution of 0.7 parts of terephthaloyl dichloride in 3 parts of MIBK was slowly added at approximately 60 to 70° C. to the mixture. After the addition, the mixture was reacted at 60 to 70° C. for 2 hours. Water was distilled off and approximately 2 parts of acetic anhydride was added. The mixture was then reacted for 7 hours at reflux conditions. Water was then added, the batch was refluxed for 0.5 hours and then the MIBK was distilled off. Approximately 1 part of 50% NaOH solution was then added and the reaction mixture was cooled, filtered and dried to give 2,2'-p-phenylenebis(3,1-benzoxazin-4-one).

Example 2

Pilot Plant Preparations of 2,2'-p-phenylenebis(3,1-benzoxazine-4-one) with Purified Isatoic Anhydride Two pilot plant batches of 2,2'-p-phenylenebis(3,1-benzoxazine-4-one) were prepared according to the procedure in Example 1.

Examples 3 to 6

Yellow Index and Sodium Concentration Measurements of 2,2'-p-phenylenebis(3,1-benzoxazinone) Samples The YI for Examples 1 and 2, and Comparison examples 1A and 1B were measured according to the Yellow Index Measurement Procedure described above. The sodium concentration for these samples were measured by Inductively Coupled Plasma (ICP) elemental analysis. The results for these measurements are shown in Table 1 below.

TABLE 1

YI and Sodium Concentration Measurements

| Example | Preparation Example | Yellow Index | Na$^+$ Conc. (ppm) |
|---|---|---|---|
| 3 | 1 | −2.6 | <1 |
| 4 | C-1A | 27.7 | 17 |
| 5 | C-1B | −15.0 | 220 |
| 6* | 2 | −13.4 | <5 |

*Example 6 measurements were the average of the 2 batches

The results demonstrate that the benzoxazinone compound samples produced by the process of the present invention (Examples 3 and 6) have lower sodium levels, and lower YI than the prior art products.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A compound of Formula I:

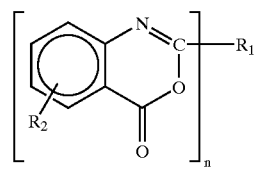

wherein n is 1 to 3, $R_1$ is a direct bond or a hydrocarbon residue having a valence of n which may further contain an heteroatom, and $R_2$ is hydrogen, halo, nitro, $C_1$ to $C_8$ alkyl, $C_1$ to $C_8$ alkoxy, or $C_1$ to $C_8$ alkenyloxy, and wherein said compound has a yellow index less than about 0, and a sodium concentration less than about 50 ppm.

2. The compound of claim 1 wherein $R_2$ is hydrogen and $R_1$ is a substituted or unsubstituted aromatic residue which may further contain a heteroatom.

3. The compound of claim 2 wherein n is 2.

4. The compound of claim 3 wherein $R_1$ is a phenylene, diphenylene or a naphthylene.

5. The compound of claim 4 wherein $R_1$ is a p-phenylene.

6. The compound of claim 1 wherein the yellow index is less than about −5.

7. The compound of claim 1 wherein the yellow index is less than about −10.

8. The compound of claim 1 wherein the sodium concentration is less than about 20 ppm.

9. The compound of claim 1 wherein the sodium concentration is less than about 5 ppm.

10. A compound of Formula I:

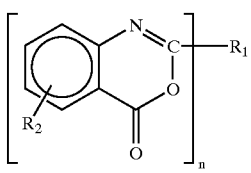

wherein n is 2, $R_1$ is phenylene, $R_2$ is hydrogen, and wherein said compound has a yellow index less than about −5, and a sodium concentration less than about 50 ppm.

11. The compound of claim 10 wherein said sodium concentration is less than about 20 ppm.

12. The compound of claim 12 wherein said yellow index is less than −10, and said sodium concentration is less than about 5 ppm.

13. A process for preparing the compound of claim 1 comprising the step of reacting a purified isatoic anhydride with approximately stoichiometric amounts of an acylating compound selected from the group consisting of carboxylic acid anhydride and acyl halide, wherein the purified isatoic anhydride is purified by extraction, sublimation or re-crystallization.

14. The process of claim 13, wherein a reaction medium is used to at least partially dissolve the isatoic anhydride.

15. The process of claim 14, wherein purified isatoic anhydride is purified by re-crystallization.

16. The process of claim 15 wherein the reaction medium is a tertiary amine.

17. The process of claim 16 wherein said tertiary amine is pyridine.

18. The process of claim 16 wherein acylating compound is an acyl halide.

19. The process of claim 18 wherein the acyl halide is an aromatic acyl halide.

20. The process of claim 19 wherein said aromatic acyl halide is selected from the group consisting of terephthaloyl dichloride, 4,4'-diphenyldicarboxylic acid dichloride and naphthalene-2,6-dicarboxylic acid dichloride.

21. The process of claim 19 wherein said aromatic acyl halide is terephthaloyl dichloride.

* * * * *